United States Patent [19]
Thorn

[11] Patent Number: 5,961,556
[45] Date of Patent: *Oct. 5, 1999

[54] PROSTHETIC SUSPENSION UNIT HAVING ELASTOMERIC ENERGY STORAGE UNITS

[75] Inventor: Richard P. Thorn, Erie, Pa.

[73] Assignee: Lord Corporation, Cary, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/775,544

[22] Filed: Dec. 31, 1996

[51] Int. Cl.⁶ .................................. A61F 2/74; A61F 2/82
[52] U.S. Cl. ........................ 623/27; 623/38; 92/165 PR
[58] Field of Search ................... 623/27–38, 26, 623/44; 92/165 PR

[56] References Cited

U.S. PATENT DOCUMENTS

| | | |
|---|---|---|
| 383,569 | 5/1888 | Gault . |
| 622,140 | 3/1899 | Ginn . |
| 2,559,446 | 7/1951 | Lucas et al. ................................. 3/2 |
| 2,689,351 | 9/1954 | Schindler ..................................... 3/17 |
| 3,842,443 | 10/1974 | Weber ........................................... 3/2 |
| 3,851,337 | 12/1974 | Prahl ........................................... 3/32 |
| 4,038,705 | 8/1977 | Owens et al. ................................. 3/2 |
| 4,134,159 | 1/1979 | Wilson ......................................... 3/2 |
| 4,354,397 | 10/1982 | Fix ............................................. 74/108 |
| 4,446,580 | 5/1984 | Furuya et al. ................................. 3/6 |
| 4,489,717 | 12/1984 | Moissonnier .............................. 128/80 |
| 4,578,082 | 3/1986 | Sen-Jung ................................... 623/27 |
| 4,828,186 | 5/1989 | Weiss ...................................... 248/640 |
| 4,883,493 | 11/1989 | Martel et al. ............................. 623/38 |
| 4,938,775 | 7/1990 | Morgan ..................................... 623/27 |
| 4,946,156 | 8/1990 | Hart ......................................... 272/70 |
| 5,062,857 | 11/1991 | Berringer et al. ........................ 623/25 |
| 5,133,435 | 7/1992 | Taylor ..................................... 188/381 |
| 5,133,777 | 7/1992 | Arbogast et al. .......................... 623/27 |
| 5,217,500 | 6/1993 | Phillips .................................... 623/27 |
| 5,284,352 | 2/1994 | Chen ....................................... 280/276 |
| 5,295,564 | 3/1994 | Stadelmann ............................. 188/381 |
| 5,458,656 | 10/1995 | Phillips .................................... 623/27 |
| 5,460,357 | 10/1995 | Stewart ................................... 267/294 |
| 5,464,442 | 11/1995 | Burt et al. ................................. 623/27 |
| 5,511,759 | 4/1996 | DeKraker et al. ....................... 248/575 |
| 5,580,075 | 12/1996 | Turner .................................... 280/276 |
| 5,702,488 | 12/1997 | Wood et al. ............................. 623/27 |
| 5,800,562 | 9/1998 | Wilkinson ................................ 623/27 |
| 5,800,563 | 9/1998 | Arbogast et al. ........................ 623/35 |

FOREIGN PATENT DOCUMENTS

| | | |
|---|---|---|
| 587591 | 4/1925 | France . |
| 327494 | 10/1919 | Germany . |
| 31 25 209 | 1/1983 | Germany .......................... A61F 1/08 |
| G 91 12 005 | 2/1992 | Germany . |
| 295 16 455 | 2/1996 | Germany . |
| 2 305 126 | of 0000 | United Kingdom . |
| 2 014 855 | 9/1979 | United Kingdom .............. A61F 1/04 |
| WO 93/24080 | 12/1993 | WIPO . |

*Primary Examiner*—Mickey Yu
*Assistant Examiner*—Tram A. Nguyen
*Attorney, Agent, or Firm*—Randall S. Wayland; Richard K. Thomson

[57] ABSTRACT

A prosthetic suspension unit for cushioning shocks in a prosthetic is provided. The unit includes a cylindrical sleeve attachable to a first prosthetic member; attachment member attachable to a second prosthetic member; a slide bearing allowing the attachment member to slide axially relative to the sleeve; an energy storage member cooperating between said attachment means and the sleeve; a piston positioned to slide within said sleeve and engage an axial end of the energy storage member; and anti-rotation mechanism cooperative between said sleeve and the attachment member for preventing relative rotation therebetween.

18 Claims, 3 Drawing Sheets

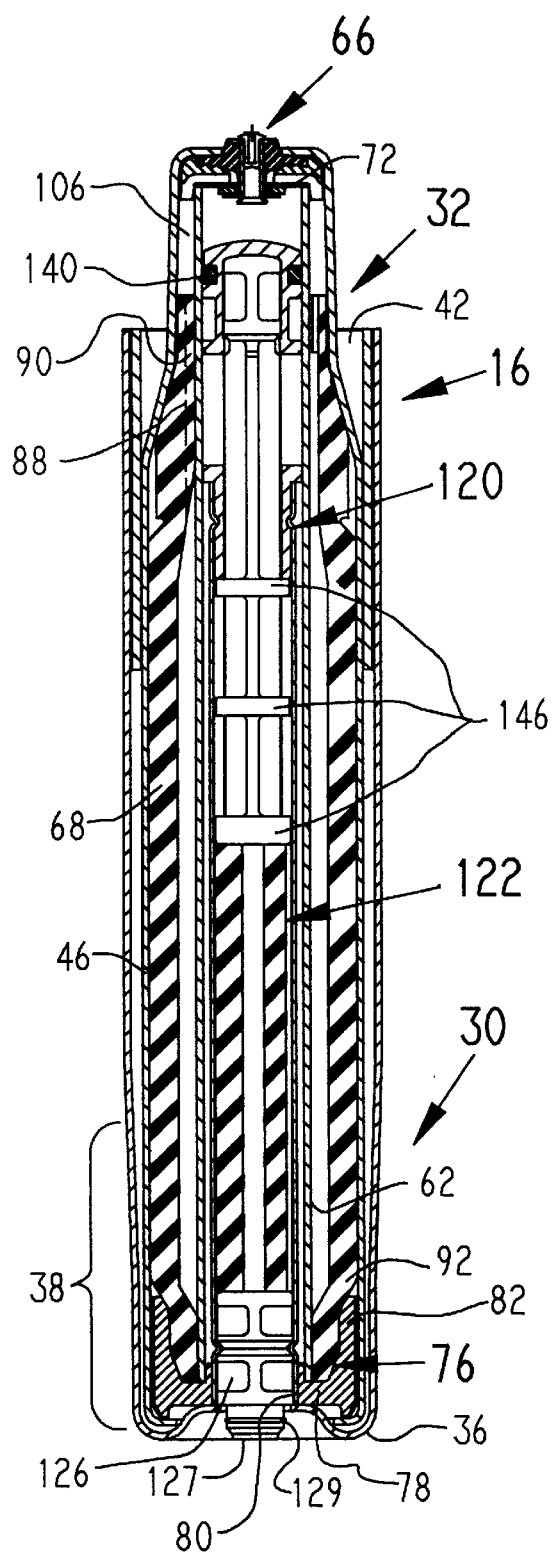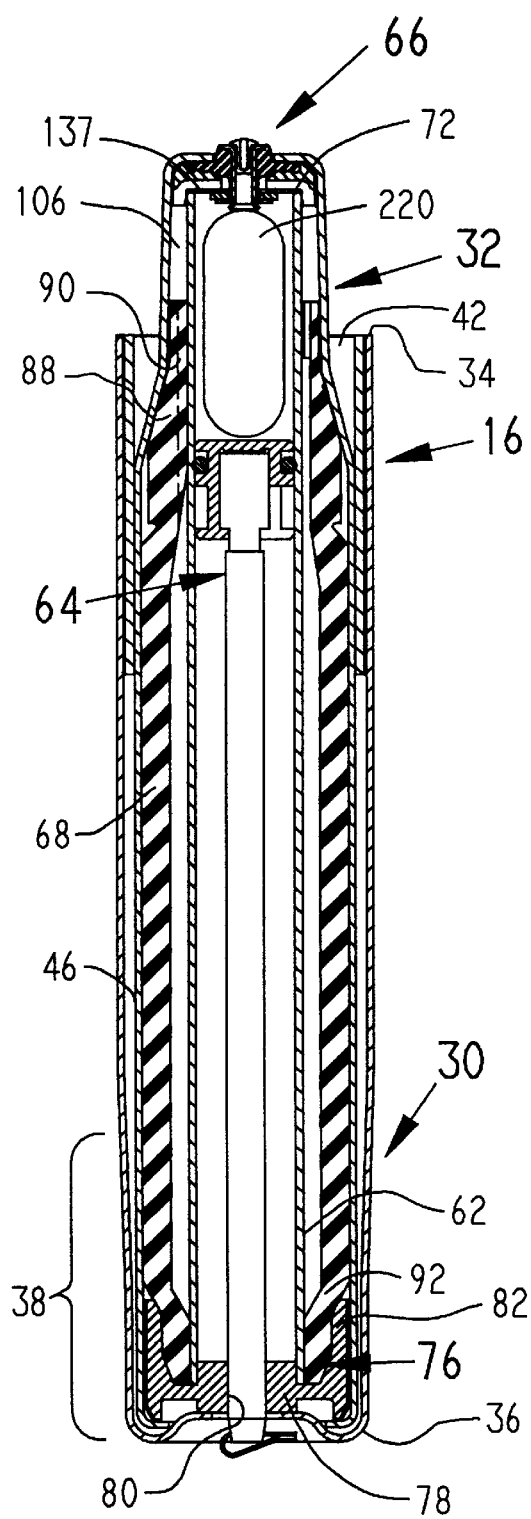
FIG. 1A
FIG. 1B (PRIOR ART)

5,961,556

PROSTHETIC SUSPENSION UNIT HAVING ELASTOMERIC ENERGY STORAGE UNITS

BACKGROUND AND SUMMARY OF THE INVENTION

This invention is directed to a linear energy management unit or cush. More particularly, the present invention is directed to an energy management unit having a long stroke. This cush is an improvement over that which is described and claimed in U.S. Pat. No. 5,511,759 entitled "Hydraulic Chair Height Adjustment Mechanism" in which the assignee of the present invention has an interest, which is hereby incorporated by reference.

In the above cited patent, a closed-cell microcellular urethane foam member which is coated with a fluid-impervious urethane material is placed in the fluid compartment of a seat height adjustment device. An elastomeric bladder is used to store energy and to raise the seat to a fully extended position from which adjustment can be made. The hydraulic fluid used in the adjustment mechanism is incompressible and would provide anyone sitting in the chair a jolt or shock. The purpose of the cush is to provide a softer feel, to effectively cushion the system such that when a person is first seated in the chair, the incompressible fluid can compress something other than his or her backside.

There are several problems with this type of cush. Firstly, it is limited in its ability to effectively cushion a load, i.e., it has a short stroke. Secondly, there is no possibility to preload the cush. This is important as adjustable height chairs are brought into regulatory compliance. Current test standards require that the chair be able to have adjustability over a given stroke length when loaded with a weight of 130 lbs. Without the benefit of a preload, the seat will sag under load and additional stroke length will need to be afforded resulting in added component length and added expense. Thirdly, repeated cycling in the fluid environment results in some of the cells of the cush collapsing further reducing the cushioning effectiveness of the device.

In order to make the energy management unit more effective, as well as more versatile, i.e., capable of use in other applications, a significant re-thinking of the cush was necessary. The preferred embodiments of the present design provide an energy management unit that is a self-contained capsule which can simply be inserted into the system with which it is used. The elastomeric portions of the cush are isolated from the hydraulic fluid of the host system so that costly coatings can be avoided. Further, the present cush design is a linear device with an extended stroke to provide significantly greater cushioning than was previously possible.

A relatively unstable, collapsible elastomeric member is provided with. guide means throughout its length (either circumferential or longitudinal). This elastomeric member is confined within a cylindrical sleeve to stabilize its movement. One end of the sleeve is plugged and the other end is provided with a slidable piston. The elastomeric member may be precompressed a desired amount (for the seat height adjuster application, by an amount sufficient to offset the 130 lb. weight). A protruding piston head can be provided with an O-ring to provide a sealing engagement with an inner cylinder which houses the capsulized cush to isolate the elastomeric member from the working fluid. The guide means engages the internal surface of the guide tube and provides damping of movement between the piston and the guide tube. A second embodiment for non-fluid applications is also provided. Adjustment capability for the precompression of the elastomeric means can be provided for appropriate applications.

Other features, advantages and characteristics of the present invention will become apparent after a reading of the following detailed description of the preferred embodiments.

BRIEF DESCRIPTION OF THE DRAWINGS

The following figures depict the preferred embodiments of the present invention, like items bearing like reference numerals and, in which FIG. 1A is a partial cross-sectional side view of a first embodiment of the energy management unit of the present invention in a seat height adjuster;

FIG. 1B is a partial cross-sectional side view of a prior art seat height adjuster with the cush the present invention is designed to replace;

DETAILED DESCRIPTION OF THE PREFERRED EMBODIMENTS

Figure 1C:
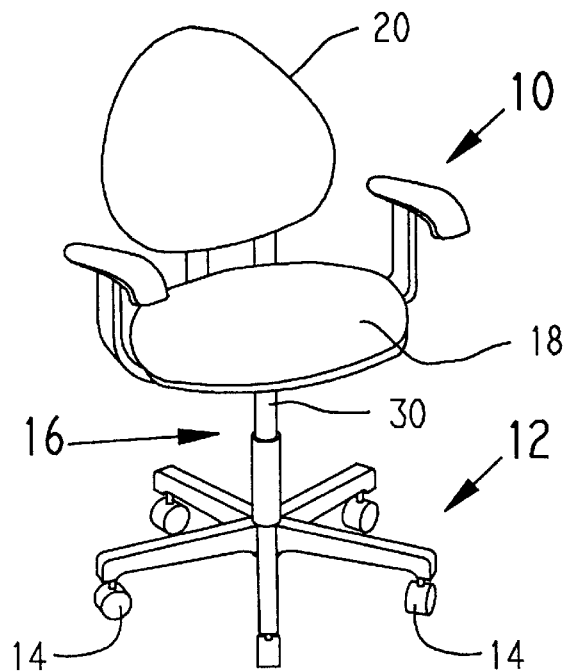
FIG. 1C is an adjustable seat height chair in which the present invention can be used.
Figure 2B:
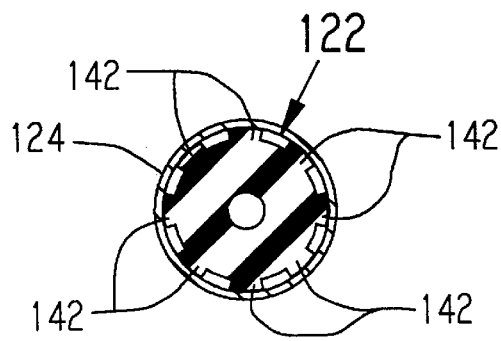
FIG. 2B is an end view of one embodiment of the energy storage device of the present invention.
Figure 2C:
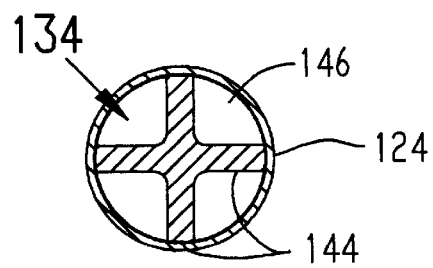
FIG. 2C is a cross-sectional end view of the piston rod taken along line 2C—2C in FIG. 2A.
Figure 2A:
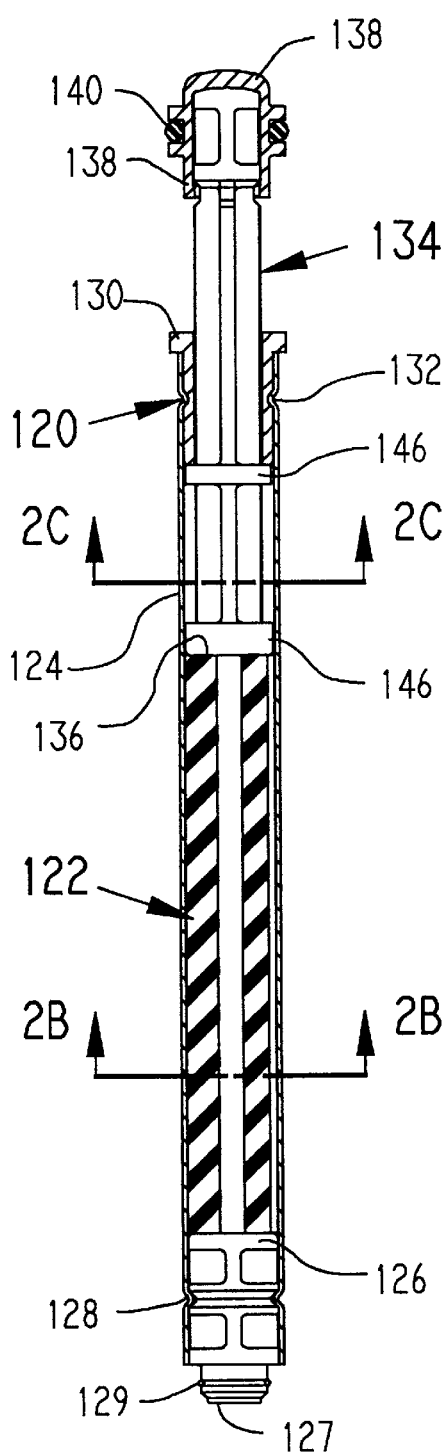
FIG. 2A is a partial cross-sectional side view of a second embodiment of the energy management unit of the present invention.

A first embodiment of the energy management unit of the present invention is shown in FIG. 1A, with a slight variation shown in FIG. 2A, generally at 120. FIG. 2A shows the cush 120 itself while FIG. 1A depicts it in use in a seat height adjuster 16. As seen in FIG. 1C, chair 10 includes a pedestal 12 which is supported on casters 14. Seat height adjustment mechanism 16 is housed in support tube 30, while chair 10 is provided with a cushioned seat 18 and seat back 20. Cush 120 will be described in conjunction with FIG. 2A.

Cush 120 includes relatively unstable, collapsible elastomeric means 122 which is contained within cylindrical sleeve 124. Cylindrical sleeve 124 provides elastomeric means 122 with controlled, stable deflection. One end of sleeve 124 is closed by plug 126 which is secured in place by crimping sleeve 124 as at 128. The opposite end of sleeve 124 is closed by a cylindrical collar 130 which is similarly held in place by crimping sleeve 124 as at 132. A first end of piston rod 134 extends through collar 130 and engages an upper end 136 of elastomeric means 122. A second end of piston rod 134 has a piston head 138 formed thereon with an O-ring 140 extending thereabout for sealingly engaging an inner cylinder 62.

As best seen in FIG. 2B, elastomeric means 122 is provided with guide means in the form of longitudinal ribs 142 running the length of the elastomeric means 122. The radially outermost surface of guide means 142 will be provided with a lubricant to reduce wear. The collapse of elastomeric means 122 into contact with the inner surface of sleeve 124 will produce damping to relative motion between piston rod 134 and cylindrical sleeve 122. The elastomeric means 122 is preferably made of natural rubber, although other materials such as urethane and Hytrel plastics may be used, as well. The durometer of the material in the elastomeric means 122 preferably falls in the range of between 50 and 80.

The piston rod 134 is preferably made of a rigid plastic material and of cruciform cross section as shown in FIG. 2C, the radially extending ribs 144 providing maximum strength for minimum material usage and weight. Plug 126 will be similarly shaped. At a plurality of locations along its length, radially extending flanges 146 are provided to stabilize the piston rod 134 against canting within the sleeve 122. Depending on the desired length of the piston rod 134, either two (FIG. 2A) or three (FIG. 1A) flanges 146 will generally prove sufficient.

As can be seen in each of FIGS. 1A and 2A, the distance between lowermost surface of piston rod 134 and uppermost surface of plug 126 is fixed by crimpings at 132 and 128, respectively. The amount of preload provided the system can be adjusted by controlling the length of elastomeric means 122. It will typically be desired, for the seating application, to provide a preload equal to between 10% and 50% of the ultimate load of the elastomeric means 122 by compressing the elastomer between 5% and 40% of its uncollapsed length. As has been mentioned, the preload is necessary to prevent the seat height adjuster 16 from sagging under the specified test load, currently 130 lbs.

Comparing FIGS. 1A and 1B, it can be seen that much remains the same in the seat height adjuster 16. An outer support tube 30 receives column tube subassembly 32 in its open end 34. Subassembly 32 can move freely within tube 30 as inner support tube 46 slides within self-lubricating bearing 42. A lower portion 38 of support tube 30 tapers inwardly toward bottom 36. Cylinder 62 houses piston rod assembly 64 and has an open upper end 72. Valve mechanism 66 is attached to the upper end of support tube 46 and seat washer 137 closes open upper end 72 of cylinder 62. Valve mechanism controls the flow of hydraulic fluid to and from inside cylinder 62 from and to space 106 and, subsequently, into expandable bladder 68 through openings 90 in upper end 88. By storing the hydraulic fluid in the expandable bladder 68, energy is saved to lift the chair to its fully extended position for subsequent re-adjustment End cap 76 includes a hub portion 78, which has a throughbore 80, and a cylindrical skirt 82 which captures lower end 92 of bladder 68.

As can be seen by comparing FIGS. 1A and 1B, the cush 120 of the present invention replaces and performs the functions of both cush 220 and piston 64. Plug 126 has an extension 127 that includes an annular recess that receives a retaining ring 129 that engages the lower surface of bottom 36 so that cush 120 is secured to support tube 30 and moves therewith, just as piston 64 did in the previous device of U.S. Pat. No. 5,511,759. Valve 66 still controls the flow of fluid to and from inside cylinder 62 from and to inside bladder 68 through space 106. O-ring 140 seals the hydraulic fluid in space 106 out of cush 120 and, hence, protects elastomer 122 from contact with such fluid. In the cush 120 of the present invention, a reduced amount of hydraulic fluid is required and the fluid flow is shielded from possible interference from the internal cush.

Figures 3A, 3B:
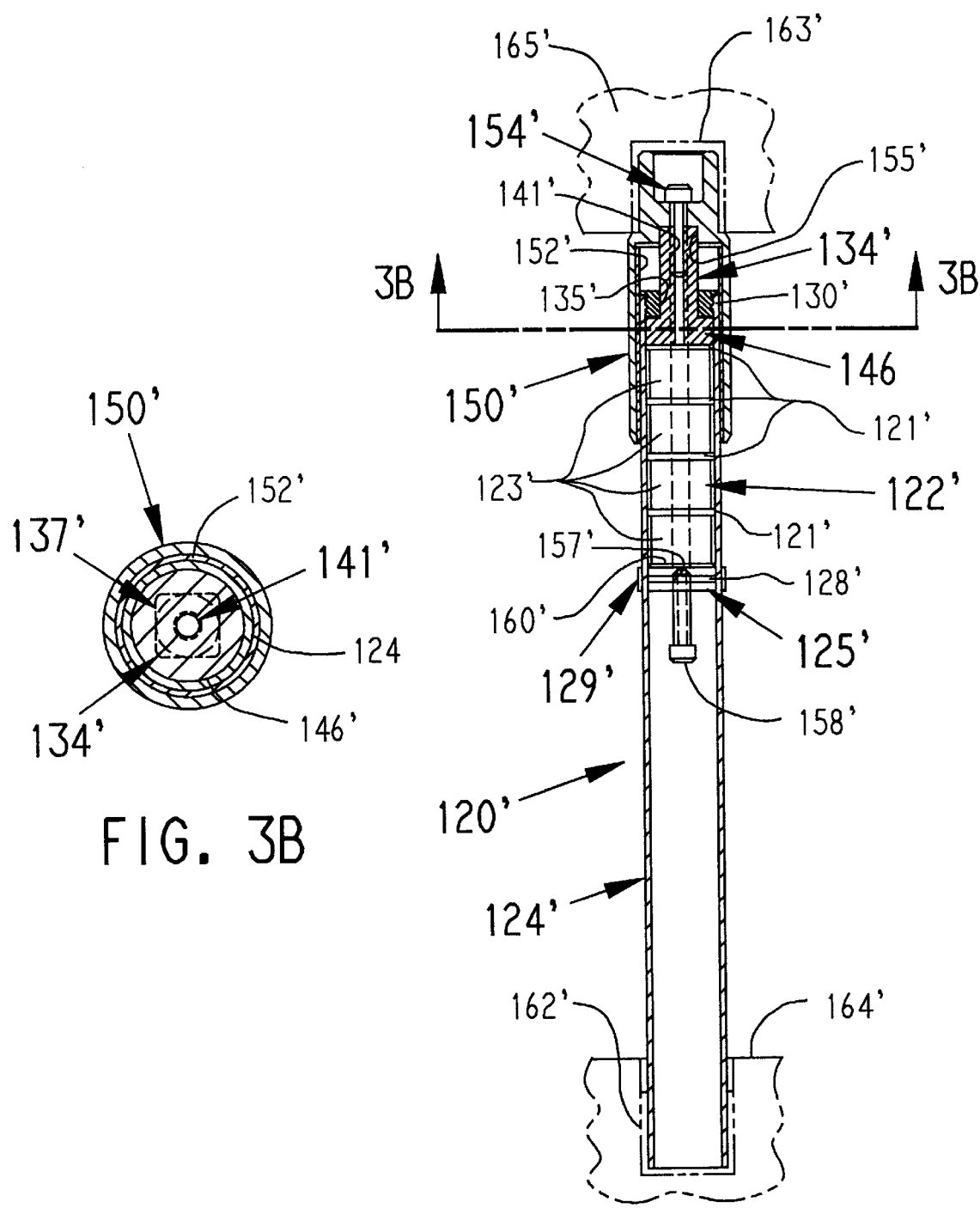
FIG. 3A is a cross-sectional side view of a third embodiment of the energy management unit of the present invention for a different application.
FIG. 3B is an end view of the piston used in this third embodiment.

A third embodiment of the cush of the present invention is shown in FIG. 3A generally at 120'. Sleeve 124' is stopped at one end by plug 125', sleeve 124' being crimped at 128' to secure the plug 125' in the desired position. Sleeve 124' is provided with a reinforcement ring 129' in those applications where sleeve 124' is a structural member. In this embodiment, the elastomeric means 122' is made up of a plurality of generally cylindrical units 123'. Each cylindrical unit has a radially extending flange 121', the plurality of flanges 121' fitting snugly in sleeve 124' and serving as the guide means in this embodiment. This elastomeric means 122', like its predecessor, is inherently unstable. The close fitting sleeve 124' provides means to stabilize the collapse of the elastomer by its piston 134'. The opposite (upper) end of sleeve 124' is closed by cylindrical collar 130' which slidingly receives piston rod 134', piston head 146' engaging the upper end of elastomeric means 122'. The majority of the length of piston rod 134' has a square configuration (FIG. 3B) which is received in a like shaped opening 135' in cylindrical collar 130'.

A cylindrical external attachment means 150' is received over the upper end of sleeve 124'. A slide bearing 152' is received by the internal periphery of attachment means 150' to facilitate relative axial movement of attachment means 150' to sleeve 124'. An axial bore 141' through piston rod 134' is threaded and receives a fastener 154'. This fastener 154' secures attachment means 150' to piston rod 134', with a cylindrical portion 137' of piston rod 134' being received in a similarly shaped recess 155'. Piston rod 134' will move concurrently with external attachment means 150' to collapse elastomeric means 122', with square shaft in square opening 135' preventing relative rotation between sleeve 124' and attachment means 150'. For appropriate applications, plug 125' can have a bore 157' that is threaded to receive an adjustment bolt 158'. Bolt 158' bears against washer 160' and by adjusting its position relative to plug 125', the amount of precompression of elastomeric means 122' can be varied. (This feature would preferably not be added to the leg prosthesis application, disclosed herein, in order to avoid user tampering which could result in personal injury.)

One potential application for this third embodiment is as a prosthetic leg. Prosthetic limbs lack some of the resiliency their natural counterparts have and make walking more difficult. By employing the cush 120' of the present invention, the resiliency provided by various components of the leg is effectively restored. In use, the cush 120' as shown in FIG. 3A will be received in adapters 162' in prosthetic foot 164' and 163' in stump cap 165'. Lower and upper ends of cush 120' are received in, for example, 31 mm adapters manufactured by Hosmer US identified by part no. 39504. It will be understood that the specified adapter is regarded as merely exemplary and that the cush 120' of the present invention could be configured to operate with other adapters, as well. In addition, the cush of the present invention is not limited to application with seat height adjusters and leg prostheses, but can be used in a variety of other applications where energy management is desired.

Various changes, alternatives and modifications will become apparent to one of ordinary skill in the art following a reading of the foregoing specification. It is intended that all such changes, alternatives and modifications as fall within the scope of the appended claims be considered part of the present invention.

What is claimed is:

1. In a leg prosthesis, an improved suspension unit comprising
    (a) a sleeve attachable to a first prosthetic member;
    (b) an external cylindrical attachment means attachable to a second prosthetic;
    (c) a slide bearing operative between said attachment means and said sleeve such that said attachment means may slide freely in an axial direction relative to said sleeve;

(d) elastomeric energy storing means positioned within said sleeve;
(e) a piston axially immovable relative to said attachment means and positioned to slide axially within said sleeve to engage an axial end portion of said elastomeric energy storing means; and
(f) anti-rotation means engaged between said sleeve and said attachment means and preventing relative rotation therebetween;

whereby said elastomeric energy storage means will provide a cushioning action to a prosthetic user.

2. A prosthesis suspension unit of claim 1 wherein said elastomeric energy storing means is relatively unstable and has a collapsible elastomeric element having a length which is substantially longer than a width.

3. A prosthesis suspension unit of claim 2 wherein said elastomeric element includes means for guiding said elastomeric element positioned along said length which are in slideable contact with an interior surface of said sleeve.

4. A prosthesis suspension unit of claim 1 wherein said elastomeric energy storing means is positioned entirely within said sleeve.

5. A prosthesis suspension unit of claim 1 wherein said elastomeric energy storing means further comprises a plurality of stacked units.

6. A prosthesis suspension unit of claim 1 wherein a portion of said attachment means surrounds said sleeve.

7. A prosthesis suspension unit of claim 1 wherein said sleeve is attachable to a prosthetic ankle and extends a major portion of a distance between said prosthetic ankle and a cap fitted to a wearer's stump.

8. A prosthesis suspension unit of claim 1 wherein said elastomeric energy storing means has a second axial end portion opposite said first axial end portion, said prosthesis suspension unit further including a support member disposed in said sleeve adjacent said second axial end portion.

9. In a leg prosthesis, an improved suspension unit comprising
(a) a sleeve attachable to a first prosthetic member;
(b) an external cylindrical attachment means attachable to a second prosthetic member;
(c) a slide bearing operative between said attachment means and said sleeve such that said attachment means may slide freely in an axial direction relative to said sleeve;
(d) elastomeric energy storing means positioned within said sleeve;
(e) a piston operative with said attachment means and positioned to slide axially within said sleeve to engage an axial end portion of said elastomeric energy storing means;
(f) anti-rotation means engaged between said sleeve and said attachment means and preventing relative rotation therebetween; and
(g) means for axially precompressing said elastomeric energy storing means;

whereby said elastomeric energy storage means will provide a cushioning action to a prosthetic user.

10. In a leg prosthesis, an improved suspension unit comprising
(a) a sleeve attachable to a first prosthetic member;
(b) an external cylindrical attachment means attachable to a second prosthetic member;
(c) a slide bearing operative between said attachment means and said sleeve such that said attachment means may slide freely in an axial direction relative to said sleeve;
(d) elastomeric energy storing means positioned within said sleeve;
(e) a piston operative with said attachment means and positioned to slide axially within said sleeve to engage an axial end portion of said elastomeric energy storing means;
(f) anti-rotation means engaged between said sleeve and said attachment means and preventing relative rotation therebetween; and
(h) wherein said anti-rotation means are integral with said slide bearing;

whereby said elastomeric energy storage means will provide a cushioning action to a prosthetic user.

11. A prosthesis suspension unit attachable between first and second prosthetic members, comprising:
a) a sleeve attachable to first prosthetic member;
b) attachment means surrounding at least a portion of said sleeve and attachable to a second prosthetic member;
c) a slide bearing interactive between said attachment means and said sleeve such that said attachment means may slide freely in an axial direction relative to said sleeve;
d) an unstable elastomeric column positioned entirely within said sleeve;
e) a piston having first and second opposed ends, said first end contacting said attachment means and said second end contacting an axial end portion of said unstable elastomeric column, said piston operative with said attachment means and slideable within said sleeve to axially displace said axial end portion relative to said sleeve and thereby compress said unstable elastomeric column; and
f) anti-rotation means operative between said sleeve and said attachment means for preventing relative rotation therebetween;

whereby said prosthesis suspension unit will provide an axial cushioning action to a prosthesis user.

12. A prosthesis suspension unit of claim 11 wherein said unstable elastomeric column has a second axial end portion opposite said first axial end portion, said prosthesis suspension unit further including a support member disposed in said sleeve adjacent said second axial end portion.

13. A prosthesis suspension unit attachable between first and second prosthetic members, comprising:
a) a sleeve attachable to a first prosthetic member;
b) attachment means attachable to a second prosthetic member;
c) slide means allowing axial sliding motion between said attachment means and said sleeve;
d) elastomeric means for energy storage cooperating between said attachments means and said sleeve;
e) means operative with said attachment means to engage an axial end portion of said elastomeric means; and
f) anti-rotation means integral with said slide means and operative between said sleeve and said attachment means for preventing relative rotation between said sleeve and said attachment means;

whereby said prosthesis suspension unit will provide an axial cushioning action to a prosthesis user.

14. A prosthesis suspension unit of claim 13 wherein said elastomeric means has a second axial end portion opposite said first axial end portion, said prosthesis suspension unit further including a support member disposed in said sleeve adjacent said second axial end portion.

15. A prosthesis suspension unit attachable between first and second prosthetic members, comprising:
   a) a sleeve attachable to said first prosthetic member;
   b) attachment means attachable to said second prosthetic member;
   c) a slide means between said attachment means and said sleeve such that said attachment means may slide axially relative to said sleeve;
   d) means for energy storage cooperating between said attachment means and said sleeve;
   e) a piston operative with said attachment means, said piston engaging an axial end portion of said means for energy storage; and
   f) anti-rotation means integral with said slide means and operative between said sleeve and said attachment means for preventing relative rotation therebetween;
whereby said prosthesis suspension unit will provide an axial cushioning action to a prosthesis user.

16. A prosthesis suspension unit of claim 15 wherein said means for energy storage has a second axial end portion opposite said first axial end portion, said prosthesis suspension unit further including a support member disposed in said sleeve adjacent said second axial end portion.

17. A prosthesis suspension unit-attachable between upper and lower prosthetic members, comprising:
   a) a sleeve of substantially constant diameter along its length attachable to said lower prosthetic member;
   b) an attachment member attachable to said upper prosthetic member, said attachment member having a cylindrical portion receiving a portion of said sleeve;
   c) means allowing relative axial sliding between said cylindrical portion of said attachment member and said portion of said sleeve;
   d) elastomeric means for energy storage housed entirely within said sleeve;
   e) a piston axially immovable relative to said attachment member and slideable within said sleeve and engaging an axial end portion of said elastomer means; and
   f) anti-rotation means operative between said sleeve and said attachment member for preventing relative rotation therebetween;
whereby said prosthesis suspension unit will provide an axial cushioning action to a prosthesis user.

18. A prosthesis suspension unit of claim 17 wherein said elastomer means has a second axial end portion opposite said first axial end portion, said prosthesis suspension unit further including a support member disposed in said sleeve adjacent said second axial end portion.

* * * * *